United States Patent
Alkubaisi et al.

(10) Patent No.: US 9,198,434 B1
(45) Date of Patent: Dec. 1, 2015

(54) METHOD OF INHIBITING PLANT VIRUS USING GOLD NANOPARTICLES

(71) Applicant: KING SAUD UNIVERSITY, Riyadh (SA)

(72) Inventors: Noorah Abdulaziz Othman Alkubaisi, Riyadh (SA); Nagwa Mohamed Mohamed Amin Aref, Riyadh (SA); Awatif Ahmed Hendi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/497,271

(22) Filed: Sep. 25, 2014

(51) Int. Cl.
*A01N 59/16* (2006.01)
*B82Y 99/00* (2011.01)
*B82Y 5/00* (2011.01)

(52) U.S. Cl.
CPC . *A01N 59/16* (2013.01); *B82Y 5/00* (2013.01); *Y10S 977/773* (2013.01); *Y10S 977/81* (2013.01); *Y10S 977/902* (2013.01)

(58) Field of Classification Search
None
See application file for complete search history.

(56) References Cited

U.S. PATENT DOCUMENTS

2004/0139494 A1* 7/2004 Yang et al. .............. 800/279
2012/0108425 A1 5/2012 Gnanamangai et al.

OTHER PUBLICATIONS

Tourney et al (2007) Nature Nanotechnology. 2: 295-300 and Supp 1-7.*
Nair et al (2010) Plant Science 179: 154-163.*

* cited by examiner

*Primary Examiner* — Steven Bernacki
(74) *Attorney, Agent, or Firm* — Richard C. Litman

(57) ABSTRACT

The method of inhibiting a plant virus using gold nanoparticles is a method of inducing plant resistance against viral disease caused by Barley Yellow Mosaic Virus (BYMV) particles by introducing a therapeutically effective amount of polydispersed gold nanoparticles to the plant through a mechanical abrasive, wherein the average effective diameter of the nanoparticles is between about 0.5 nm and 200 nm and wherein the gold nanoparticles are present at a concentration of about $1.0 \times 10^{-5}$ g/ml to about $6 \times 10^{-4}$ g/ml, and wherein the gold nanoparticles melt and dissolve the virus particles.

5 Claims, 7 Drawing Sheets

The Macrominerals Calcium (Ca$^{++}$) Levels in Justo Cultivar

- 1-Standard 30: 27.991
- 2-BYDV Control: 26.646
- 3-BYD Pure Virus: 32.331
- 4-BYDV Nano + Virus: 23.165
- 5-BYDV Virus then Nano: 33.123
- 6-BYDV Nano then Virus: 28.698
- 8-BYDV Nano then Virus diluted: 27.758

Concentration (Mg/L) vs Treatments

Fig. 7

METHOD OF INHIBITING PLANT VIRUS USING GOLD NANOPARTICLES

BACKGROUND OF THE INVENTION

1. Field of the Invention

The present invention relates to agri-nanotechnology, and particularly to a method of inhibiting a plant virus using gold nanoparticles, specifically, the application of gold nanoparticles in melting and inhibiting Barley Yellow Dwarf Virus (BYDV) in barley.

2. Description of the Related Art

Barley (*Hordeum vulgare*) is mainly cultivated and used for a staple human food in the kingdom of Saudi Arabia (KSA). It ranks third after wheat and sorghum in grain production, and the annual yield is about 118.5 thousand tons of grain. Barley yellow dwarf virus (BYDV) is one of the most economically important viral diseases of barley, which is transmitted by aphids. BYDV is differentiated from many other plant virus diseases because it is not transmitted by rubbing (mechanical inoculation).

Nanotechnology is considered today to make substantial contributions to sustainable development by improving practices in the fields of agriculture, industry, healthcare (both human and animal), and environmental protection. The successful application of various nano-platforms in medicine under in vitro conditions has generated some interest in agri-nanotechnology. Agri-nanotechnology holds the promise of the controlled release of agrochemicals and site-targeted delivery of various macromolecules needed for improved plant disease resistance, efficient nutrient utilization, and enhanced plant growth.

At present, resistance to wheat mosaic, barley yellow dwarf, wheat streak mosaic, and wheat spindle streak (or wheat yellow mosaic) is of major importance. No single barley variety is resistant to all major diseases. Severe losses in the production, quality and safety of wheat and barley crops have resulted in a major financial distress for farmers. This is because the affected crops are often unsuitable for marketing, and so must be channeled to lower value feed markets. It has been acknowledged that breeding for the resistance to this disease is the most desirable solution, but the genetics of resistance are very complicated and difficult to manipulate. There is an immense interest in understanding the molecular processes involved in virus assembly.

Gold nanoparticle (GNP) interactions with DNA can perform antisense gene regulation via hybridization with the mRNA of interest, thereby preventing protein production. That is, the DNA gold nanoparticles bind to a target mRNA strand and prevent translation into proteins via steric inhibition of the ribosome by the gold nanoparticle. Application of nanoparticle technology in plant pathology provides new ways for crop protection. Therefore, it would be desirable to use gold nanoparticles to identify potential or possible remedies to BYDV or in the identification of resistant genes within the biological cell system to improve plant resistance against viral infection.

Thus, a method of inhibiting a plant virus using gold nanoparticles solving the aforementioned problems is desired.

SUMMARY OF THE INVENTION

The method of inhibiting a plant virus using gold nanoparticles comprises introducing a therapeutically effective amount of polydispersed gold nanoparticles to the plant using a mechanical abrasive, wherein the average effective diameter of the nanoparticles is between about 0.5 nm and 200 nm, wherein the gold nanoparticles are present at a concentration of about $5.0 \times 10^{-5}$ g/ml to about $5 \times 10^{-4}$ g/ml, and wherein the gold nanoparticles surround and "melt" or kill the virus particles. Additionally, a method of transmitting plant virus particles into a plant host is described, which comprises directly contacting virus particles using a mechanical abrasive on leaf surfaces of the plant host.

These and other features of the present invention will become readily apparent upon further review of the following specification and drawings.

BRIEF DESCRIPTION OF THE DRAWINGS

FIG. 7 is a graph illustrating the concentration of calcium ($Ca^{++}$) in Justo cultivar in different treatments of virus-like particles (VLPs) and gold nanoparticles (GNPs).

Similar reference characters denote corresponding features consistently throughout the attached drawings.

DETAILED DESCRIPTION OF THE PREFERRED EMBODIMENTS

Figure 1:
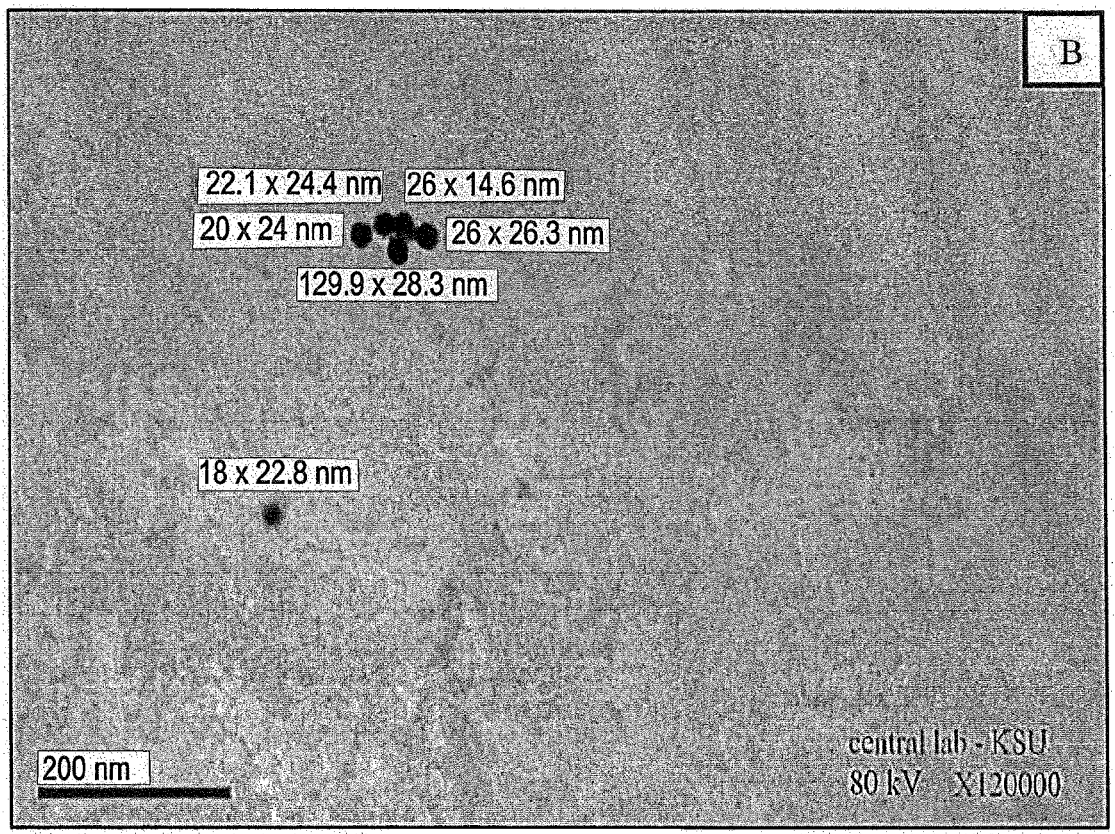
FIG. 1 is a Transmission Electron Micrograph (TEM) showing the sizes of GNPs (gold nanoparticles) used in a method of inhibiting a plant virus using gold nanoparticles.

The method of inhibiting a plant virus using gold nanoparticles, and particularly the application of gold nanoparticles to enhance plant virus resistance against Barley Yellow Dwarf Virus (BYDV) or to kill the virus, which is a dangerous pathogen of winter barley, is described. As illustrated in detail below, ultrastructure studies by transmission electron microscopy (TEM) of treated plants indicate the promising application of gold nanoparticles (GNPs) in inducing plant virus resistance in barley. The following examples will further illustrate the invention but are not to be construed as limiting its scope.

Example 1

Method of Preparing Gold Nanoparticles [(Au) NPs]

The gold nanoparticles were made from the Turkevich method using citrate ion as a reducing agent. A sample of $5.0 \times 10^{-6}$ mol of $HAuCl_4$ was dissolved in 19 ml of deionized water (the result should be a faintly yellowish solution), and then heated until it boiled. Heating was continued while stirring vigorously and 1 ml of 0.5% sodium citrate solution was added. Stirring was continued for the next 30 minutes, which results in a wine-red color. Reduction in the amount of sodium citrate will reduce the amount of the citrate ions available for stabilizing the particles, which will cause the small particles to aggregate into bigger ones (until the total surface area of all particles becomes small enough to be covered by the existing citrate ions). Thus, to achieve small and active particles the amount of citrate ions must be reduced. The above method for preparation of spherical gold nanoparticles generally produces modestly mono disperse spherical gold nanoparticles suspended in water of around 10-20 nm in diameter.

The size of the gold nanoparticles (GNPs) was measured using transmission electron microscopy (TEM). Mono dispersed drops of the gold nanoparticles were placed on a carbon-coated Formvar grid for two minutes. Then it was examined with a JEOL 1220 transmission electron microscope. The TEM revealed the actual size of prepared gold particles directly, from 10-30 nm.

Example 2

Characterization of the Prepared Gold Nanoparticles (GNPs) According to Zeta Sizer and Zeta Potential Five preparations of gold nanoparticles (GNPs) were tested for size distribution report by intensity using Zeta sizer for Malvern (ZEN3600). As well as four of them were applied for zeta potential. In preparation No. 5, the GNPs were diluted from the original prep. No. (4) to (1 vol.: 2 vol.) so (400 µl from the GNPs: 800 µl of distilled water) compared to the original one. Five solutions were prepared for various studies, having the following particle size distributions: a first solution of 1.585-23.60 nm; a second solution of 1.465-26.14 nm; a third solution of 3.151-31.67 nm; a fourth solution of 3.744-66.74 nm; and a fifth solution of 3.225-118 nm.

Zeta sizer has been used to characterize and determine the size and size distribution of the synthesized GNPs. Two solutions were prepared for nano applications in the studied plants in the greenhouse of this study to evaluate the biological distribution of differently size of GNPs and to study the effect of size particles and biological distribution of GNPs to enable their diverse applications in Nanotechnology for preventing the viral infection. The GNPs first prepared solution had two kinds of particles depending on the size. The smallest and finest one has 3.225 nm in diameter while the other one is 118 nm. Zeta potential reflected their properties for their potential charge, which was positive for the most active one with free dispersed particle that had 87.6 mV, while the other peak had 35.1 mV potential. The first solution was illustrated two hetero peaks distributed by their size that explained two kinds of spherical gold particles aggregation diameters of 1.585 and 23.60 nm and with intensities of 27.2 and 72.8% respectively. Zeta potential charts exhibited only one pointed end peak that means free active homogenized zeta potential with negative charge of 41.6 mv.

The second solution exhibited its criteria with very small size distributed in two peaks, one of them has a diameter of 1.465 nm and the other has 26.14 nm. Both of them are well dispersed with intensity of 14.7 for former and 85.3 for the latter. The second solution had two different peaks with sizes 3.151 and 31.67 nm, respectively, with different intensity 75.3% for the former and 24.7% for the latter. The third solution had very different peaks value, depending on their sizes, which determined and scattering of light intensity. The smallest and finest one has 3.744 nm in diameter with 10.5% intensity value, while the other one has 66.74 nm with 89.5% intensity value. Zeta potential showed the characteristics of the GNPs No. 5 represented in the three peaks with different values with less dispersed clarified in the negatively charged. These values are; 12.8, 26.9 and 44.5 mV, respectively.

The GNPs diameters ranged to their sizes distribution in the following preparations: (a) 1.585 to 23.60 nm, (b): 1.465 to 26.14 nm, (c): 3.151 to 31.67 nm, (d): 3.225 to 118 nm and (e) 5: 3.744 to 66.74 nm.

Example 3

Virus Cultivation and Propagation Using Abrasive Sandpaper for Mechanical Transmission into Barley Plants

*Hordeum vulgare* (Barley) cultivars were cultivated in a greenhouse. The barley leaves were inoculated with the virus (BYDV) particles using abrasive sandpaper on the lower blade and then sprayed by water and left for ten days for symptomotology. The symptoms on barley were highly variable and appeared after approximately (14 days/two weeks) from mechanical inoculation. The yellowing of the leaves is the typical model of the viral disease symptoms.

Figure 2:
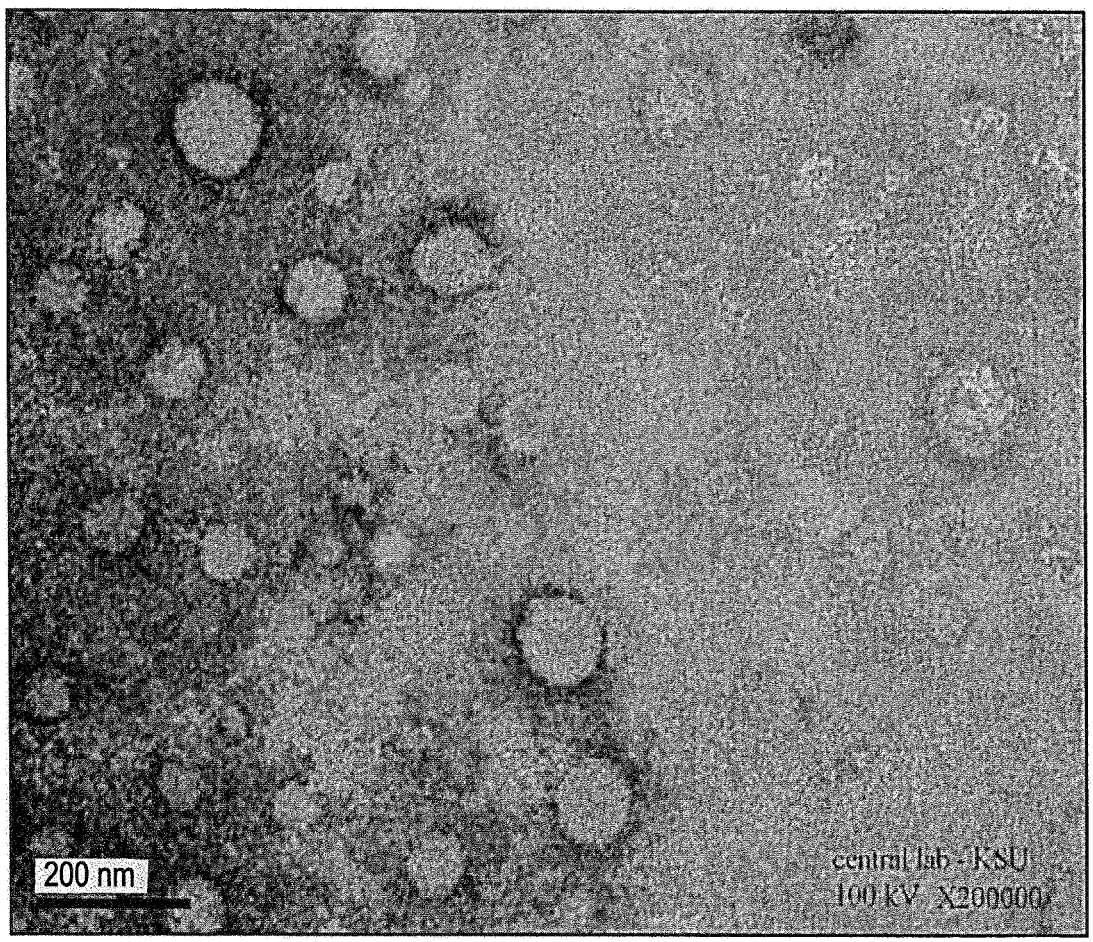
FIG. 2 is a TEM of purified barley yellow dwarf virus (BYDV) particles.

BYDV virus was purified from barley cultivar to be tested for the trials. The plants were propagated and infected with virus source. The purification was followed as conducted by literature methods with slight modification. Transmission electron micrograph (TEM) revealed that the actual size for this virus particle is around 25-30 nm (see FIG. 2). ELISA test (Enzyme-Linked Immunosorbent Assay) indicates that barley was sensitive to be detected in ELISA test from leaf extracts. Virus productivity indices were 0.540 at a wavelength of 405 nm. Deferential centrifugations analyses were applied for the virus purification, depending on our result from the purification of the virus in Barley cultivar from the infected leaves, which was 27.30 g of leaves that had a maximum yield of 0.62 mg/ml of virus particles. The BYDV particles were successfully transmitted by a novel mechanical method using abrasive sandpaper to the plant system of barley as a susceptible host in *Hordeum vulgare* host. FIG. 2 is a representative TEM of the virus particles, which display clean uniform sizes of about 30 nm.

Example 4

Method of Applying Gold Nanoparticles (GNPs) on the Barley Plants to Reach its Potent Efficacy The active gold nanoparticles (GNPs) were mixed with the identified BYDV particles in crude sap, then inoculated inside the plant leaves mechanically to have treatment No. 1 (neutralization). The same source of BYDV virus was inoculated using an abrasive sandpaper, followed with the GNPs by sterile cloth sheath to have treatment No. 2 (pre-treatment). While in treatment No. 3, the leaves of barley were wiped by GNPs first then the same source of virus was used to inoculate the plant using abrasive sandpaper (post-treatment) and then followed by the GNPs only. Then the leaf samples were examined by TEM to observe the effect of GNPs en route to viral damages.

Example 5

In Vitro Incubation of GNPs with Purified BYDV Particles

Figure 3:
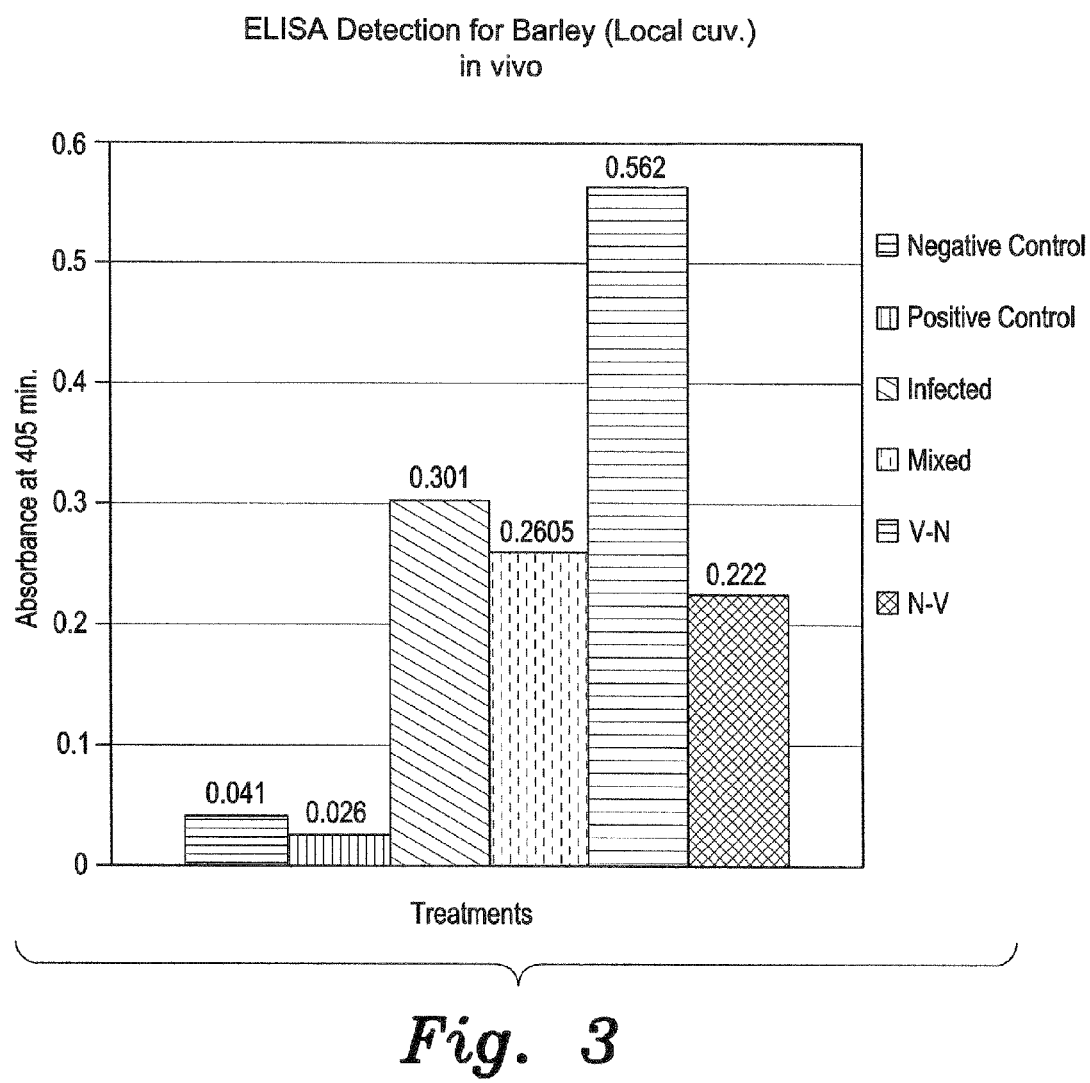
FIG. 3 is a chart showing an example of enzyme-linked immunosorbent assay (ELISA) detection results for Barley yellow dwarf virus in vivo under different treatment protocols.
Figure 4:
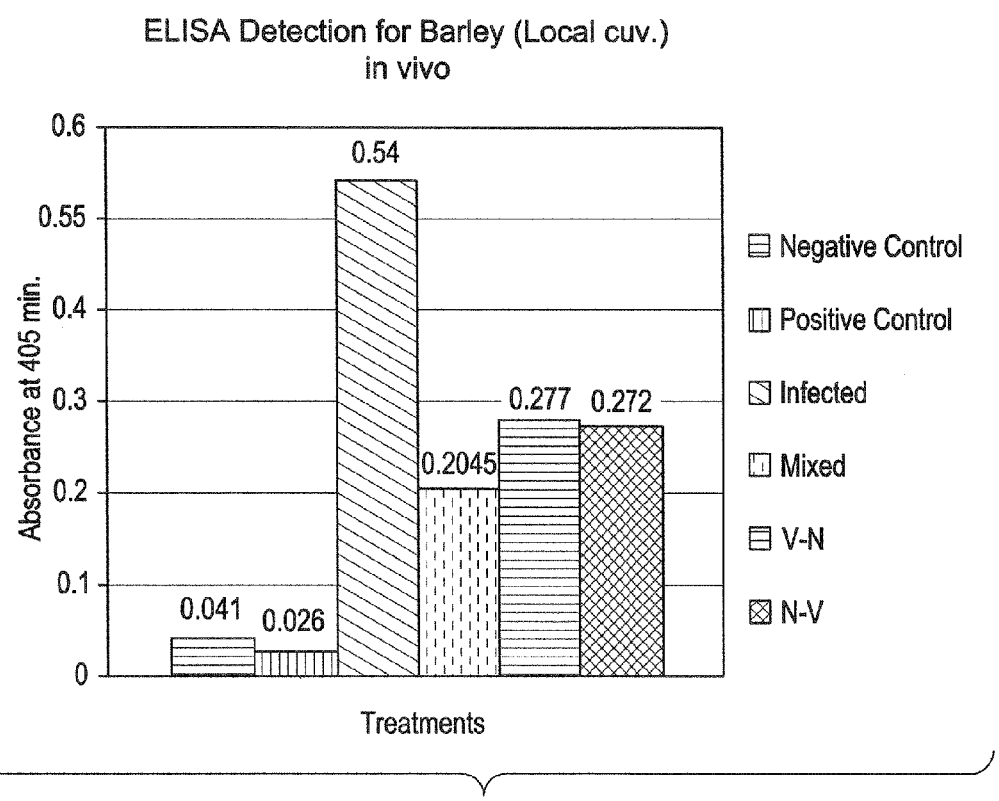
FIG. 4 is a chart showing another example of enzyme-linked immunosorbent assay (ELISA) detection results for Barley yellow dwarf virus in vitro under different treatment protocols.
Figure 5:
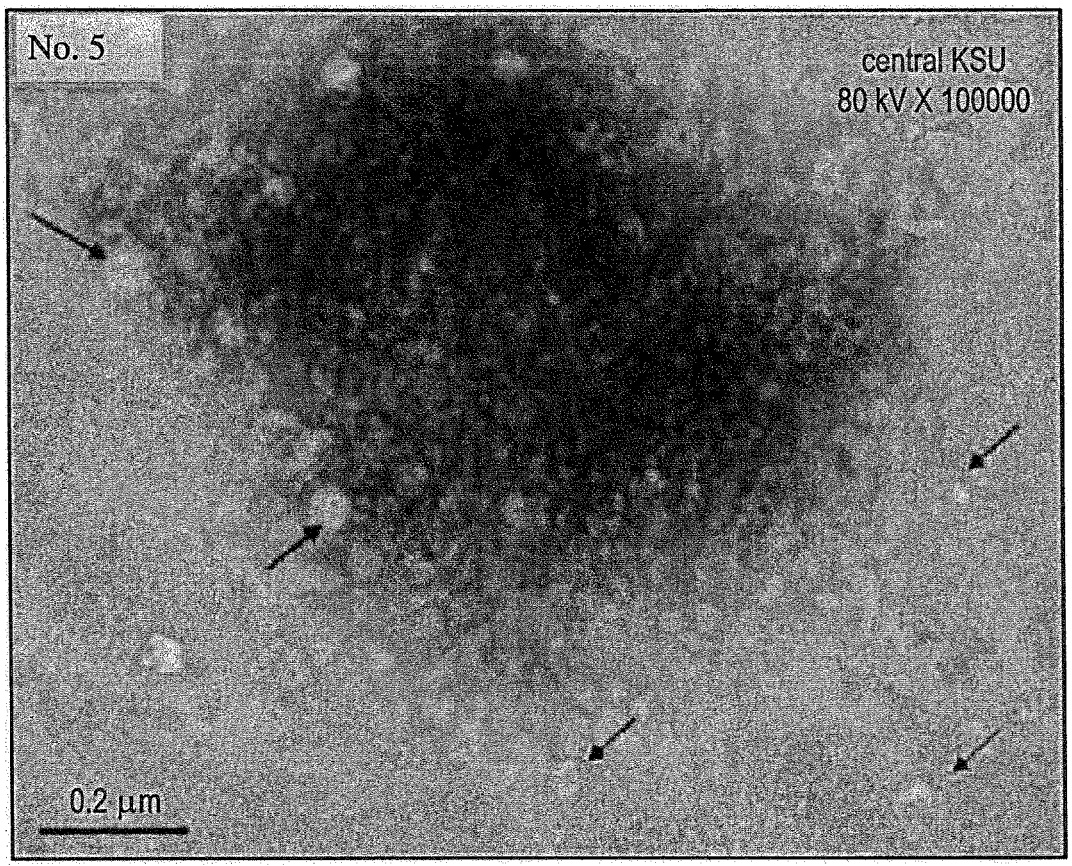
FIG. 5 is a TEM of a virus-like particle (VLP) being surrounded by GNPs in vitro.
Figure 6:
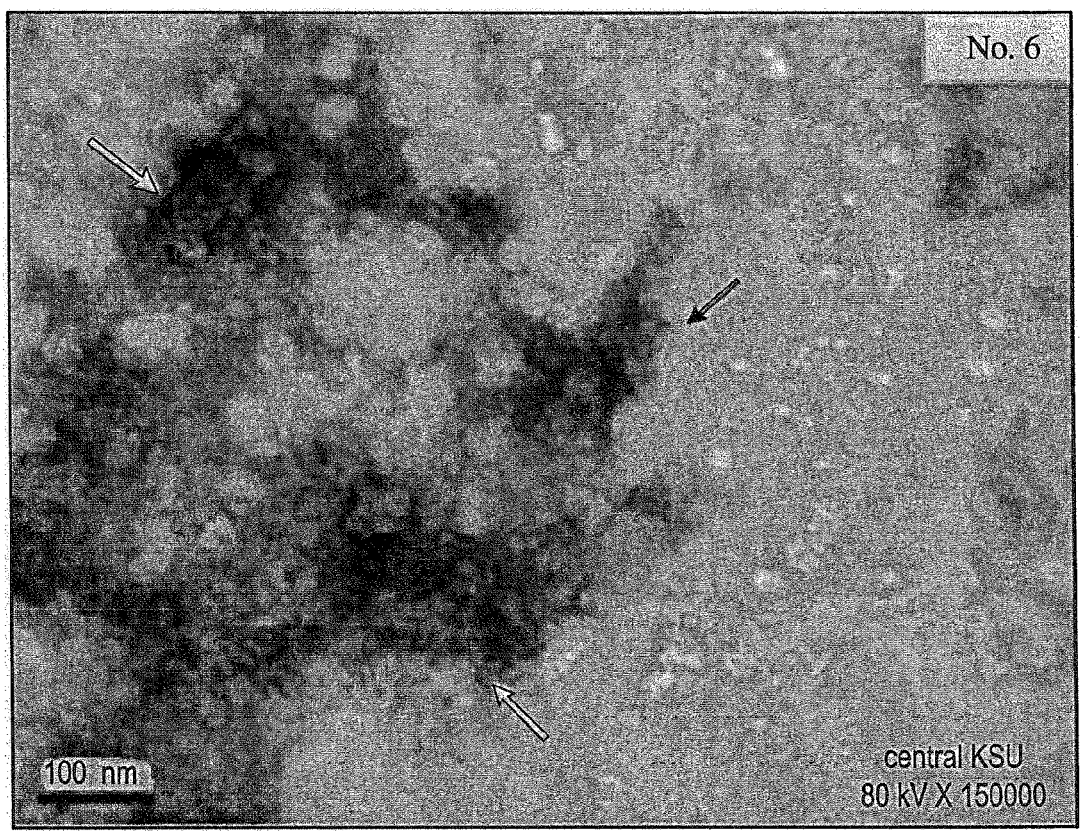
FIG. 6 is a TEM of virus-like particles (VLPs) mixed with GNPs after being incubated for 24 hours in vitro.

The gold nanoparticles (GNPs) were first incubated with the purified virus particles in vitro using three different incubation periods of time: (i) zero time of incubation, (ii) 24 hours, and (iii) 48 hours, respectively. Second, different concentrations of GNPs were used. FIG. 3 shows the ELISA (Enzyme-Linked Immunosorbent Assay) detection of Barley in vivo. FIG. 4 shows ELISA detection of barley in vitro. TEM showed that the GNPs surround non damaged (virus like particles) VLPs (virus-like particles), as shown in FIG. 5. After incubation for 24 hrs the shapes of some VLPs were deformed and damaged.

Example 6

Cytological Alterations in Barley Plants Treated with GNPs First, then with Viral Particles (In Vivo)

Double infection from gold nanoparticles followed by BYDVs caused different changes inside the cells. TEM shows the a twisted invagenated shape of cell wall, and plasmodesmata in some parts of cell wall that was so tendered showing the cytoplasmic membrane in it, and at a higher magnification, showing some cytoplasmic contents beside this. Proteinous contents were also located along the cell wall, very dark particles from GNPs showed an accumulation with VLPs inside it. Basically, the micrographs showed a highly twisted cell wall from the double effects, with a lot of dark GNPs embedded and accumulating in the cell wall, accompanied by VLPs. Finally, it was found that that VLPs and GNPs gathered in the cytoplasm in circulated unregulated shapes having borders occupying the whole lumen of the cytoplasm.

The extremely small size of nanoparticles means they exhibit enhanced or different properties when compared with the bulk material. The extremely small size of nanoparticles results in the particles having a large surface area relative to their volume, as well as when nanoparticles are applied on leaf surfaces, they enter through the stomatal openings or through the bases of trichomes and then translocated to various tissues.

The most important moment of plant virus entry taking in a consideration is that of inducing viral infection crossing the cell wall barriers. In our study, we knocked out and interfered with virus as a bio nano particles with another metal GNPs on plant leaf surface or pushing them together into plant cell system and following up the events of systemic plant defense. Especially, when the study succeeded to induce BYDV infection mechanically on the surface of barley leaves.

Concerning the studied cultivar (Justo and Local), the application of GNPs revealed a potential damage on VLPs according to five determinant factors that play an important role for viral particles deformation. First, time duration for the incubation period with virus particles; 24 hours and 48 hours. The 48-hour incubation period exhibited highly deformation and vanishing VLPs both in vivo and in vitro.

Regarding the concentration and toxicity of gold nanoparticles, the inventors found that the original concentration of 0.00034 gm of original GNPs 1 ml of water that had great effect on VLPs compared to using the diluted 0.00017 gm of GNPs in 1 ml of water. Additionally, the results indicate that using these low concentrations of GNPs had no toxicity effect on plants.

In our data we could rely in this result as a benefit of reverse such phyto toxicity of GNPs by mixing it with virus particles as protein and nucleic acid component to enhance their applicability and effectiveness for virus control. Gold nanoparticles are mainly used in biotechnology and biomedicine. Their optical absorption spectrum, affinity to thiol groups, and toxicological innocuousness are the main properties that predestine gold nanoparticles for diagnostical and therapeutical applications.

The application of GNPs particles on the local and Justo cultivar had a great damaging result on virus particles in TEM as an application of GNPs before virus infection. This could explain the interaction performance in our results, which had different degrees between VLPs and GNPs, illustrated as clotting, surrounding, integration, and accumulation particles. This kind of interval molecular interactions could lead to disappearing and/or swelling, smashing, deformation, corrosive and puffiness of infected virus particles.

GNPs sizes, the smallest size of GNPs has potential dramatic effect in our method as; GNPs prep. 2-1.465 to 26.14 nm. Moreover, these assemblies can be produced with atomic precision and are ideal monodisperse, nanometric building blocks that can aid in the study of molecularly directed assembly of biomolecular arrays.

The data indicates that combining virus particles with GNPs possibly leads to synergistic therapeutic effects for inducing virus resistance by the interaction performances, as illustrated by the TEMs. Prior studies have shown that the modified GNPs inducing gene regulation upon entry to the cytoplasm of the cell the DNA where the GNPs can bind to the strand, preventing translation of the mRNAs corresponding protein.

TEM showed that many filamentous strands bind with GNPs crossing the cell wall. Colloidal gold particles can be attached to many traditional biological probes, such as antibodies, lectins, superantigens, glycans, nucleic acids and receptors. Particles of different sizes are easily distinguishable in electron micrographs, allowing simultaneous multiple-labelling experiments. In in vitro analysis, gold nanoparticles are used to locate viruses, bacteria or proteins in many rapid tests, making use of their characteristic red color. This effect is well known, e.g., from pregnancy tests, cocaine tests or cancer tests. In our in vivo applications, gold nanoparticles can be used in picture-giving procedures for localization as well as diagnosis, and hyperthermic treatment allows the targeted destruction of cells. Outside of medical technology, the deployment of gold nanoparticles in photovoltaics by embedding them into thin solar cells has shown to increase solar energy conversion efficiencies. In the cytoplasm, the nanoparticles may bind with different cytoplasmic organelles and interfere with the metabolic processes at that site. The micrograph of treated plant with GNPs revealed a band of GNPs surrounded cell adjacent and inside the cell wall. In our study, it was noticed huge hyper polyploidy conjugated with application of GNPs.

Example 7

Amino Acid Distribution in the Wheat Plants Infected with Virus and Treated with GNPs Protein peptide content is the expression metabolic results of the predicted amino acid distributed in the whole plant with different concentrations for each Individual according to the susceptibility and resistance-response to virus infection for protecting and innate immune plant system. The inventors found distribution changes for having amino acids with high concentrations after applying GNPs compared to that with low concentration in the ones infected with virus depending on the median of statistical analysis. It means potential pathogen defense functions in response to BYDV infection. It was noticed that the whole six treatments showed highly significant differences, as shown in Table 1. Mixed treatment appears to be the best one with range (0.03763) and 0.993 Correlation, then N-V with range (0.03686), V-N with range (0.03368) compared to the Nano only (0.03997).

For Justo cultivar, the GNPs application had less significant differences, while there is no significant difference at the nano treatment only, as shown in Table 1. The same was noticed for nano application for three treatments, M (0.03085) then N-V (0.02860), V-N (0.02763) compared to the control (0.03118), and nano only (0.04498). These data were related to the correlation and the 95% Confidence Interval of the difference range. Table 1 revealed that Local is better than Justo; M is the best treatment in local and Justo.

required for callose deposition. Thus, the callose deposits append to be present in WSMV-infected wheat were presumably less extensive. Ultra-structure studies using TEM has revealed callose deposition in the middle lamella between two cells. Moreover, TEM shows a fatal alteration and virus assembly nearby and inside the cell wall and that divalent ions such as $Ca^{++}/Mg^{++}$ could aid in the stabilization of the tertiary structure of molecules of some viral proteins and its ribonucleic acid.

TABLE 1

Results of the viral infection and the effect of GNPs application on the levels of concentration for the 17 measured amino acids separated from two studied cultivars at two different treatments; early and late

| | Local Cultivar | | | | Justo Cultivar | | | | |
| --- | --- | --- | --- | --- | --- | --- | --- | --- | --- |
| | | | 95% Confidence Interval of the Difference | | | | 95% Confidence Interval of the Difference | | |
| Sig-(2-tailed) | Correlation | Lower | Upper | Range | Sig-(2-tailed) | Correlation | Lower | Upper | Range |
| C | 0.001 | 0.990 | −0.05823 | −0.01551 | 0.04272 | 0.040 | 0.980 | −0.032049 | −0.000869 | 0.03118 |
| V | 0.001 | 0.990 | −0.04533 | −0.01517 | 0.03016 | 0.028 | 0.974 | −0.026901 | −0.001769 | 0.02513 |
| M | 0.001 | 0.993 | −0.54273 | −0.16645 | 0.03763 | 0.040 | −0.976 | −0.031729 | −0.000883 | 0.03085 |
| V-N | 0.001 | 0.992 | −0.04972 | −0.01603 | 0.03368 | 0.021 | 0.978 | −0.030457 | −0.002825 | 0.02763 |
| N-V | 0.001 | 0.993 | −0.05298 | −0.01612 | 0.03686 | 0.037 | 0.979 | −0.029648 | −0.001046 | 0.02860 |
| N | 0.001 | 0.991 | −0.05661 | −0.05661 | 0.03997 | 0.0256 | 0.954 | −0.034998 | −0.009986 | 0.04498 |

Example 8

Macro Minerals ($Ca^{++}$) in the Leaf Content and its Role on the Cell Wall

Many metallic ions affect virus replication, and the key ions are identical to those needed for the synthesis of a variety of virulent secondary metabolites by cells of the particular genus. In host-virus associations, the ions of groups IIA and IIB of the periodic table are generally involved in stability of extracellular plant virions. Research has shown that the relationship between virus infection and host plant nutrition is influenced by the plant species and/or cultivar, virus strain, time of inculcation, place of inculcation, plant part samples, and time of sampling. Some research has shown that lower contents of $Ca^{++}$ in wheat plants infected with Wheat Streak Mosaic Virus (WSMV). However, here $Ca^{++}/Mg^{++}$ content in the infected barley plant had high values compared to healthy ones. After GNPs applications, it was noticed that the concentration of the $Ca^{++}/Mg^{++}$. This result indicates that the decrease of the ions may benefit in controlling viral infection.

FIG. 7 illustrates that the virus infection increase the calcium content in the whole shoots and roots of each plant that was 32.331 mg/l compared to control 26.646 mg/l. The highest value in all fourth gold nanoparticle GNP treatments had virus treatment and subsequently GNP treatment then N=33.123 mg/l followed by the virus infection. There was a slight difference between the two other treatments, N-V and diluted N-V, with results of 28.698 and 27.758 mg/l, respectively. On the other hand, the Mixed treatment decreased the $Ca^{++}$ content 23.165 mg/l, while all the other treatments increased the $Ca^{++}$ content.

Other research has shown that the altered ion content of cell walls in infected tissue might contribute indirectly to the weakening of its walls. Calcium is of key importance in cell wall stability in dicotyledons because it cross-links with pectin. There is very little pectin in the cell walls, and the only major effect that decreased calcium might have in terms of pectin stability is in the middle lamella. Calcium is also It is evident from the foregoing examples and discussion that in vitro experiments had more damage on virus particles compared to in vivo ones, as evidenced by the TEM and ELISA results. In addition, exposing virus particles twice to gold nanoparticles (GNPs) raveled extra damage as a double effect. According to our methods, it can be shown that using tiny prepared GNPs provide a dual potential nano-effect of vanishing pathogenic plant virus particles after incubation period of 24 and 48 hours in vitro, as well as improving plant growth criteria at the high quality level compared to healthy plants. These findings were further corroborated by data of molecular and biological parameters as well as electron micrographs, which indicated resistance against the virus infection. Thus, using tiny gold nanoparticles with diameter in the range of 1-250 nm, more specifically, 1.0 nm and 50 nm with a concentration of $1\times10^{-4}$ g/ml to about $6\times10^{-4}$ g/ml, and more specifically about $3.4\times10^{-4}$ g/ml water as an eco-friendly potential virus control agent induces highly resistant plants against BYDV with an improvement of barley horticulture quality. The use of abrasive sand paper was useful and helpful tool for transmitting BYDV diseases a first record in KSA.

Therefore, the above results show that the gold nanoparticles possess dual effects in barley plants, that of melting the virus and vanishing their particles inside and outside the plant cells without serious side effects on the plant metabolism.

It is to be understood that the present invention is not limited to the embodiments described above, but encompasses any and all embodiments within the scope of the following claims.

We claim:

1. A method of inhibiting Barley Yellow Mosaic Virus (BYMV) or Barley Yellow Dwarf Virus (BYDV) using gold nanoparticles, comprising the steps of
   a) introducing a solution consisting of a plurality of poly-dispersed gold nanoparticles suspended in water to a plant infected with BYMV or BYDV, wherein the gold nanoparticles have an average effective diameter of between 1.0 nm and 150 nm, the concentration of gold nanoparticles in the solution is about 0.00034 gm of gold nanoparticles in 1 ml of water, and b) directly applying the solution on leaf surfaces of the plant, and using a mechanical abrasive thereon; and wherein said gold nanoparticles surround and dissolve the BYMV or BYDV particles.

2. The method of inhibiting viral disease according to claim 1, wherein the plant is *Hordeum vulgare*.

3. The method of inhibiting viral disease according to claim 1, wherein the mechanical abrasive is sandpaper.

4. The method of inhibiting viral disease according to claim 3, wherein said nanoparticles enter into the plant through stomatal openings or through bases of trichome and translocate to various tissues of the plant.

5. The method of inhibiting viral disease according to claim 1, wherein the effective diameter of the gold nanoparticle is between about 1.0 nm and 50 nm.

* * * * *